US00PP27772P3

(12) United States Plant Patent
Christen

(10) Patent No.: US PP27,772 P3
(45) Date of Patent: Mar. 14, 2017

(54) PEAR TREE NAMED 'CH201'

(50) Latin Name: ***Pyrus communis* L.**
Varietal Denomination: CH201

(71) Applicant: Agroscope, Conthey (CH)

(72) Inventor: Danilo Christen, Conthey (CH)

(73) Assignee: Agroscope (CH)

( * ) Notice: Subject to any disclaimer, the term of this patent is extended or adjusted under 35 U.S.C. 154(b) by 149 days.

(21) Appl. No.: 14/544,077

(22) Filed: Nov. 20, 2014

(65) Prior Publication Data

US 2016/0150698 P1 May 26, 2016

(51) Int. Cl.
*A01H 5/08* (2006.01)

(52) U.S. Cl.
USPC ..... Plt./176

(58) Field of Classification Search
USPC ..... Plt./176
CPC ..... A01H 5/08
See application file for complete search history.

*Primary Examiner* — Keith Robinson
(74) *Attorney, Agent, or Firm* — Michelle Bos Legal LLC

(57) ABSTRACT

A new pear variety named 'CH201' is distinguished by its crunchy bicolored fruit, which maintains its quality during very long term storage, and its low susceptibility to fire blight.

5 Drawing Sheets

Latin name: *Pyrus communis* L.
Variety denomination: 'CH201'.

BACKGROUND OF THE VARIETY

'CH201' is a new and distinct variety of pear tree that originated as a product of a controlled cross made in 2000 at Conthey, Switzerland, of 'Harrow Sweet' (female parent, U.S. Plant Pat. No. 9,863) and 'Verdi' (male parent, not patented). A seedling resulting from the cross was asexually propagated by grafting in 2009 at Conthey, Switzerland, and was subsequently observed over successive asexually propagated generations. The tree and its fruit have been found to remain true to type and to retain the desirable characteristics for which the variety was selected.

'CH201' is distinguished by its crunchy bicolored fruit, which maintains its quality during very long term storage, and its low susceptibility to fire blight. 'CH201' is slightly more susceptible to fire blight than its female parent 'Harrow Sweet', but is less susceptible than 'Verdi' or 'Louise Bonne' (not patented). Fruit of 'CH201' has a coarser texture, a more pronounced blush, and longer storage ability than that of 'Harrow Sweet', 'Verdi' or 'Louise Bonne'.

BRIEF DESCRIPTION OF THE PHOTOGRAPHS

DETAILED BOTANICAL DESCRIPTION OF THE VARIETY

Figure 1:
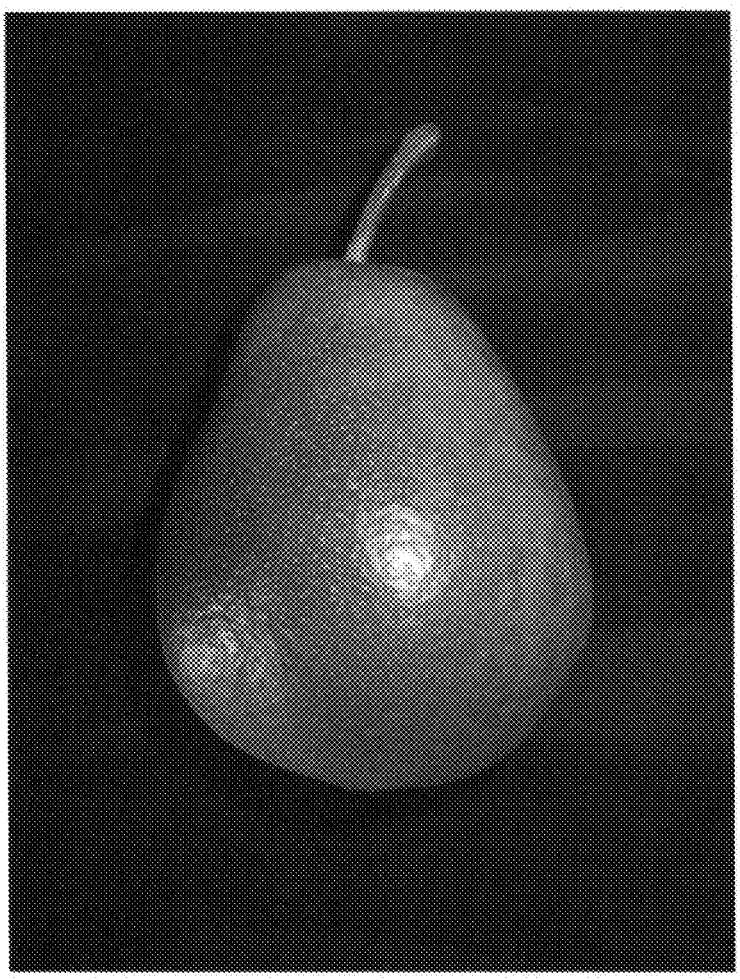
FIG. 1 is a photograph of the fruit of the variety at harvest, showing the intense red blush overcolor of the skin.
Figure 2:
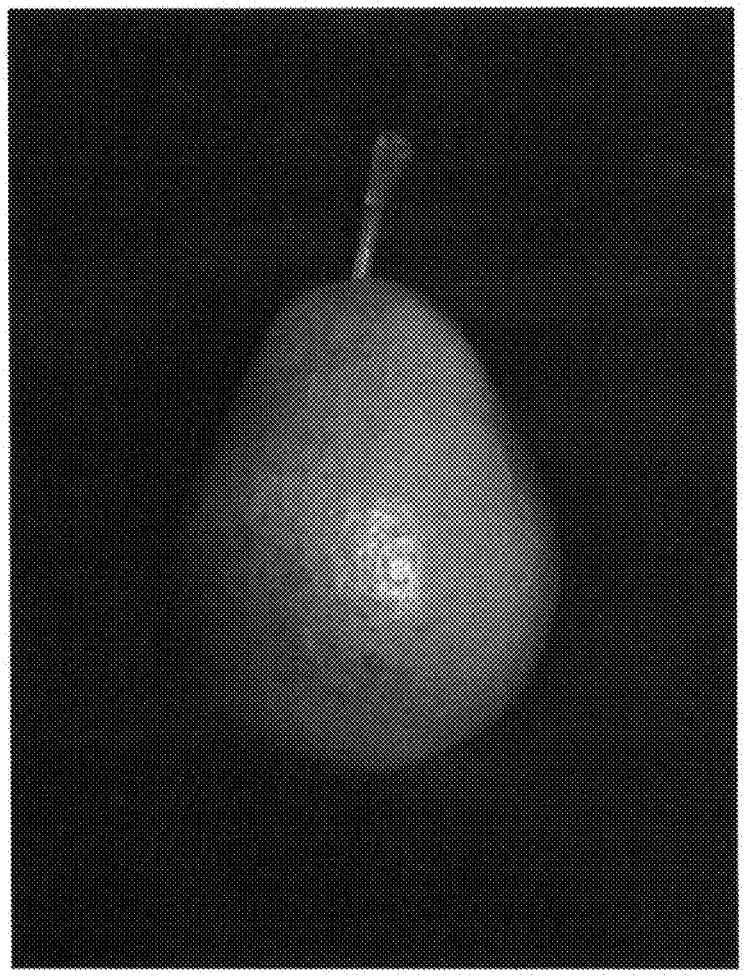
FIG. 2 is a photograph of the fruit of the variety at harvest, showing the ground color of the skin.
Figure 3:
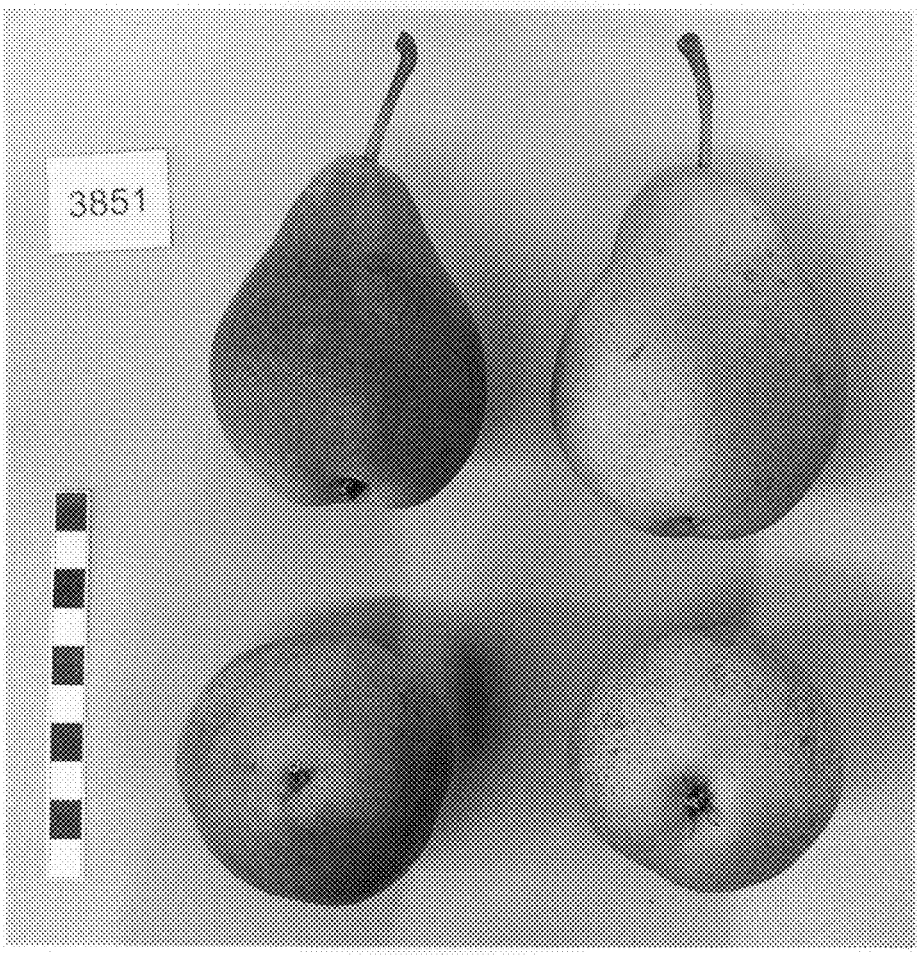
FIG. 3 is a photograph of fruit of the variety at harvest (left) and after storage (right)
Figure 4:
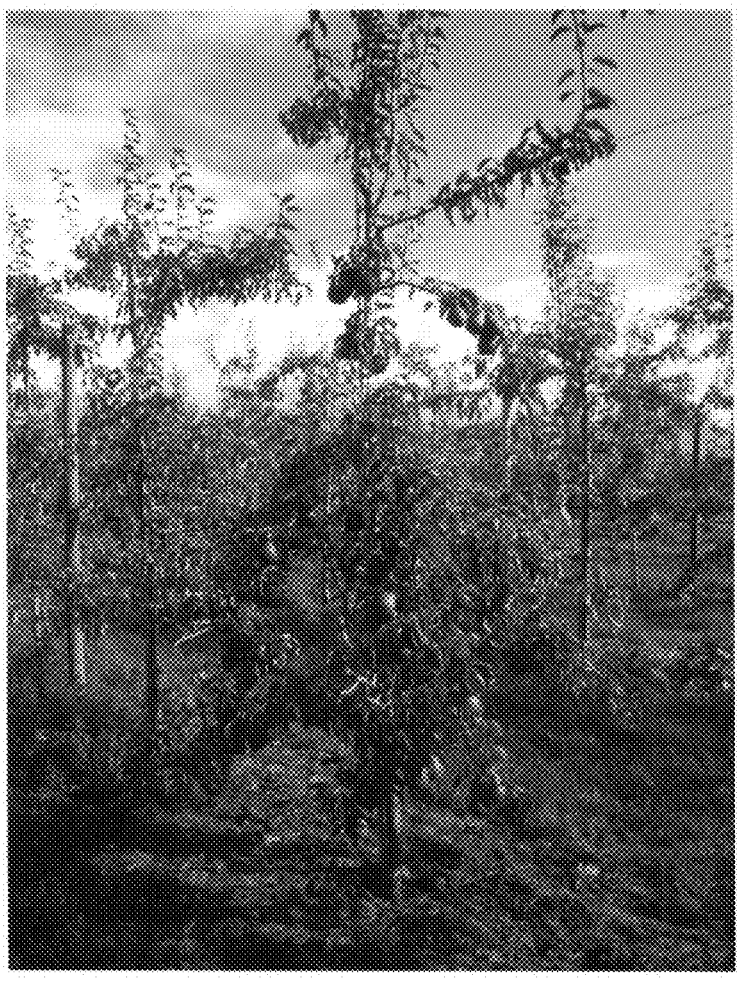
FIG. 4 is a photograph of the tree of the variety.
Figure 5:
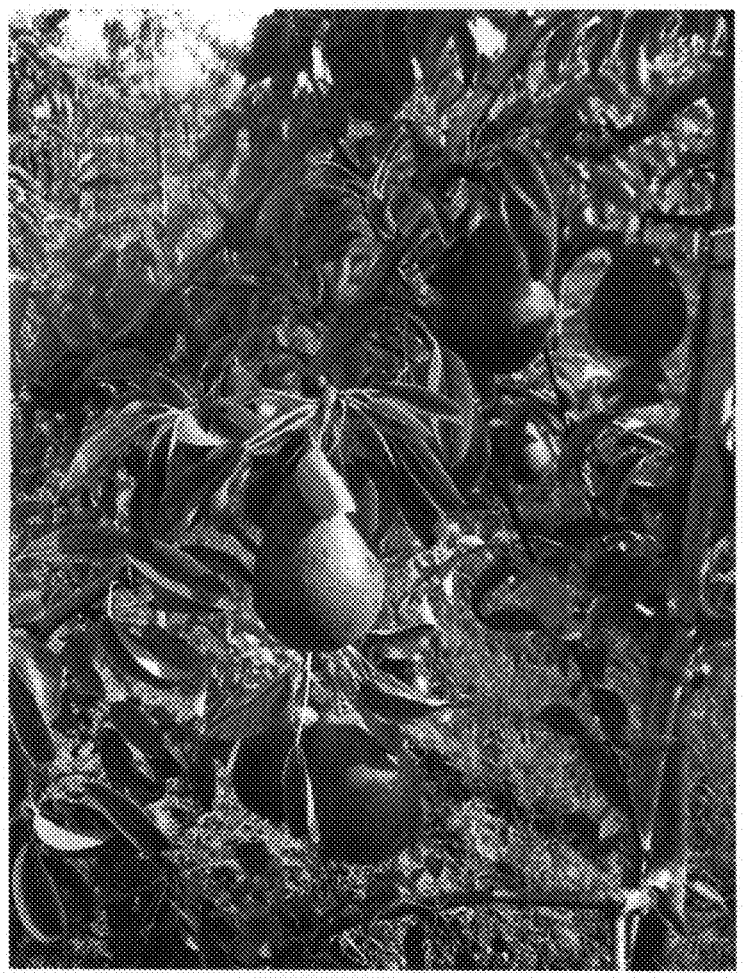
FIG. 5 is a photograph of the fruit and leaves of the variety.

The following detailed botanical description is based on observations made during the 2013 and 2014 growing seasons at Conthey, Switzerland of second- and third-leaf 'CH201' trees planted in 2011 on 'BA29' rootstock (not patented). All colors are described according to The Royal Horticultural Society Colour Chart (2007). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
- *Vigor.*—Medium-weak.
- *Type.*—Ramified.
- *Vegetative buds.*—Conical, slightly held out; greyed-orange 163A.
- *Habit.*—Drooping.
- *Height.*—2.5 m.
- *Spread.*—Medium.
- *Trunk diameter (at 30 cm above the graft).*—4.5 cm.
- *Bark texture.*—Fine.
- *Bark coloration.*—Greyed-green 196A.
- *Winter hardiness.*—Hardy in area tested.

Branch (fruiting branches located at around 1 m above the graft union):
- *Length.*—130 cm.
- *Diameter.*—1 cm.
- *Crotch angle.*—90°.
- *Bark color.*—Greyed-green 198D.

One year old shoot:
- *Length.*—20 cm.
- *Color.*—Grey-brown N199C.
- *Anthocyanin coloration of growing tip.*—Absent or very weak.
- *Pubescence.*—Weak.
- *Thickness.*—0.4 cm.
- *Internode length.*—5 cm.
- *Pubescence.*—Weak.
- *Number of lenticels.*—3 (per $cm^2$).

Flower buds:
- *Quantity per spur.*—2.
- *Shape.*—Conical.

*Length.*—1 cm.
*Diameter.*—0.8 cm.
*Color.*—Greyed-green 195A.

Flowers:
*Diameter of fully open flower.*—1.9 cm.
*Depth of open flower.*—0.6 cm.
*Relative position of petal margin.*—Not touching.
*Number per cluster.*—7.
*Date of first bloom.*—Apr. 4 (2014).
*Date of full bloom.*—Apr. 11 (2014).
*Relative timing of first bloom.*—Mid-early, similar to 'Conference' (not patented).

Petals:
*Number per flower.*—5.
*Shape.*—Round.
*Length.*—0.9 cm.
*Width.*—0.8 cm.
*Apex.*—Round.
*Base.*—Pointed.
*Margin.*—Smooth.
*Coloration of upper surface.*—White NN155C with red-purple 65A edge.
*Coloration of lower surface.*—White NN155C and red-purple 65A.

Pistils:
*Size.*—0.6 cm.
*Color.*—Yellow-green 149A.

Stigma:
*Size.*—0.1 cm.
*Color.*—Yellow-green 150A.

Style:
*Length.*—0.5 cm.
*Color.*—Yellow-green 149A.

Ovary:
*Size.*—0.2 mm.
*Color.*—Yellow-green N144C.

Anthers:
*Quantity.*—20.
*Pollen.*—Abundant; yellow 4D.
*Length.*—0.12 cm.

Pedicel:
*Length.*—3.5 cm.
*Diameter.*—0.12 cm.
*Color.*—Green 143C.

Sepals:
*Quantity.*—5.
*Color.*—Greyed-orange N170B.
*Length.*—1 cm.
*Width.*—0.3 cm.
*Shape.*—Conical pointed.
*Apex.*—Pointed Acute.
*Margin.*—Smooth.
*Attitude in relation to corolla.*—Fused at the base.

Leaves:
*Shape.*—Elliptical.
*Length.*—6.5 cm.
*Width.*—3.7 cm.
*Length/width ratio.*—1.75.
*Blade margin.*—Finely crenate.
*Apex.*—Acute.
*Base.*—Obtuse.
*Color of upper surface.*—Green 143A.
*Color of lower surface.*—Green 143B.
*Attitude in relation to shoot.*—Downward.
*Curvature of longitudinal axis.*—Medium.

Petiole:
*Length.*—4.5 cm.
*Diameter.*—0.12 cm.
*Coloration.*—Yellow 2C.
*Stipule.*—None.

Fruit:
*Quantity per cluster.*—2 to 4.
*Height.*—9 cm.
*Width.*—6.6 cm.
*Ratio of height to width.*—0.9.
*Weight.*—209 g.
*General shape in profile.*—Pyriform.
*Position of maximum diameter.*—⅓ inferior.
*Symmetry in longitudinal section.*—Total.
*Skin texture.*—Firm.
*Background color of skin before storage.*—Green 143C.
*Background color of skin after storage.*—Yellow-green 150A.
*Area of over color of skin.*—70%.
*Intensity of over color of skin.*—High.
*Color of overcolor before storage.*—Greyed-purple 185A.
*Color of overcolor after storage.*—Orange-red N30A.
*Relative area of russet around eye basin.*—Absent.
*Relative area of russet on cheeks.*—Absent.
*Relative area of russet on stalk attachment.*—Absent.
*Length of stalk.*—3.5 cm.
*Thickness of stalk.*—0.4 cm (middle).
*Curvature of stalk.*—3°.
*Attitude of stalk in relation to axis of fruit.*—Tilt 15°.
*Stalk color.*—Grey-brown N199C.
*Depth of stalk cavity.*—2 mm.
*Depth of eye basin.*—0.5 cm.
*Width of eye basin.*—1.5 cm.
*Relief of area around eye.*—Smooth.
*Attitude of sepals at harvest.*—Closed.
*Firmness of flesh at harvest.*—14.
*Firmness of flesh when ripe.*—2.78.
*Flesh texture.*—Crunchy.
*Aroma.*—Sweet pear.
*Juiciness.*—Medium juicy.
*Brix.*—11°.
*Flesh color.*—White NN155A.

Seeds:
*Quantity per fruit.*—7.
*Shape.*—Oval-oblong.
*Length.*—1 cm.
*Width.*—0.45 cm.
*Color.*—Grey-brown N199D.

Harvest:
*Time for harvest.*—Mid-September, 1 week after 'Conférence' (not patented).
*Time of maturity for consumption.*—September to April (with 7 days shelf-life at 20° C.).
*Amount of fruit produced per tree per harvest.*—14 kg ($3^{rd}$ leaf trees).

Disease resistance/susceptibility: Low susceptibility to fire blight *Erwinia amylovora* (greenhouse tested for shoot with artificial inoculation).

Market use: Fresh.

Storage characteristics: Stores well until March under NA conditions and until May under CA conditions.

I claim:

1. A new and distinct pear tree substantially as described and illustrated herein.

* * * * *